(12) United States Patent
Brasch et al.

(10) Patent No.: US 6,569,399 B2
(45) Date of Patent: May 27, 2003

(54) PROCESS FOR THE PREPARATION OF HIGH-PURITY MAGNESIUM HYDROXIDE AND MAGNESIUM OXIDE FROM MAGNESIUM ALKOXIDES

(75) Inventors: Andrea Brasch, Meldorf (DE); Klaus Diblitz, Schenefeld (DE); Kai Dölling, Pinneberg (DE); Tilo Feldbaum, Hamburg (DE); Klaus Noweck, Brunsbüttel (DE); Jan Schiefler, Hamburg (DE)

(73) Assignee: SASOL Germany GmbH, Hamburg (DE)

( * ) Notice: Subject to any disclaimer, the term of this patent is extended or adjusted under 35 U.S.C. 154(b) by 0 days.

(21) Appl. No.: 09/091,857

(22) PCT Filed: Dec. 19, 1996

(86) PCT No.: PCT/DE96/02483

§ 371 (c)(1),
(2), (4) Date: Jun. 24, 1998

(87) PCT Pub. No.: WO97/24304

PCT Pub. Date: Jul. 10, 1997

(65) Prior Publication Data

US 2002/0015677 A1 Feb. 7, 2002

(30) Foreign Application Priority Data

Dec. 27, 1995 (DE) ........................................... 195 48 863

(51) Int. Cl.⁷ ............................... C01F 5/08; C01F 5/14
(52) U.S. Cl. ........................ 423/636; 423/155; 423/635
(58) Field of Search .................. 423/636, 155, 423/635

(56) References Cited

U.S. PATENT DOCUMENTS

| | | | |
|---|---|---|---|
| 2,478,593 A | * | 8/1949 | Pike ........................... 423/636 |
| 2,920,105 A | | 1/1960 | Kluge et al. |
| 3,471,259 A | * | 10/1969 | Sese ........................... 423/636 |
| 3,657,361 A | | 4/1972 | Lenz et al. |
| 3,946,102 A | * | 3/1976 | Thomas ....................... 423/600 |
| 4,104,180 A | | 8/1978 | Burnop |
| 4,590,289 A | | 5/1986 | Albert et al. |
| 4,609,755 A | | 9/1986 | Farrar |
| 4,698,323 A | | 10/1987 | Band et al. |
| 5,023,071 A | * | 6/1991 | Sherif ......................... 423/636 |

FOREIGN PATENT DOCUMENTS

| | | |
|---|---|---|
| DE | 2112644 | 12/1971 |
| DE | 2622839 A1 | 12/1976 |
| DE | 3244972 | 2/1984 |
| EP | 0244917 A1 | 11/1987 |
| GB | 667708 | 3/1952 |
| SU | 1002243 A | 3/1983 |

OTHER PUBLICATIONS

Abstract No. 102829d, "Metal 2–methoxyethoxides," *Chemical Abstracts*, vol. 117, 1992, p. 894.

Abstract No. 180183u, "Activated alkyl–and allylalkali metal reagents: contrasting behavior towards ethylene," *Chemical Abstracts*, vol. 119, 1993, p. 729.

Abstract No. 140176z, "New molecular precursors for the formation of V–Mg multicomponent exides by sol–gel process," *Chemical Abstracts*, vol. 122, 1995, p. 482.

(List continued on next page.)

Primary Examiner—Wayne A. Langel
(74) Attorney, Agent, or Firm—Browning Bushman P.C.

(57) ABSTRACT

There is provided a process for producing high-purity magnesium hydroxide by reaction of magnesium or reactive magnesium compounds with hydroxy compounds yielding magnesium alkoxides, followed by hydrolysis to form magnesium hydroxide, or a process for producing magnesium oxide by calcination of magnesium hydroxide.

10 Claims, 3 Drawing Sheets

OTHER PUBLICATIONS

Abstract No. 314192c, "Some 2–substituted ethoxides of magnesium," *Chemical Abstracts*, vol. 120, 1994, p. 1103.

Abstract No. 181680t, "Preparation of β–(N,N–diethylamino)ethyl methacrylate," *Chemical Abstracts*, vol. 97, 1982, p. 759.

Abstract No. 59775y, "Higher alcohol acrylates and methacrylates," *Chemical Abstracts*, vol. 83, 1975, p. 39.

Abstract No. 177160s, "Metal alkoxides and preparation of composite oxides using the same," *Chemical Abstracts*, vol. 116, 1992, p. 175.

Abstract No. 39350x, "Manufactured of hardness, high–toughness, high–wear–resistance silicon nitride ceramics," *Chemical Abstracts*, vol. 123, 1995.

Item No. 15725, "Improved alkoxide production," *Research Disclosure*, No. 157, May 1977, p. 19.

W. C. Gilpin and N. Heasman, "Resources from the sea—minerals," *Chem. Ind.*, London, 1977, pp. 567–572.

J. C. Drum and S. Tangney, "Planning a Sea Water Magnesia Plant," *Trans. J. Br. Ceramic Soc.*, vol. 77, No. 4, 1978, pp. 10–14.

* cited by examiner

PROCESS FOR THE PREPARATION OF HIGH-PURITY MAGNESIUM HYDROXIDE AND MAGNESIUM OXIDE FROM MAGNESIUM ALKOXIDES

The present invention relates to a process for producing high-purity magnesium hydroxide and for obtaining therefrom magnesium oxide by calcination.

Natural resources of magnesium hydroxide [CRN 1309-48-4] are rare so that this material is seldom mined. Nowadays, magnesium hydroxide is obtained by precipitation from seawater (cf. Gilpin, W. C. and Heasman, N., *Chem. Ind.* (London), 1977, p. 567–572; Drum, J. C., Tangney, S., *Trans. J. Br. Ceramic Soc.*, 77 (1978), no. 4, p. 10–14) and precipitation from magnesium salt solutions using calcium hydroxide.

Said manufacturing processes have one disadvantage: the magnesium hydroxide produced in this way is hardly suitable for a large number of catalytic operations and for the production of special ceramics. This is primarily due to impurities in the form of other metals making the magnesium hydroxide particularly unsuitable for catalytic processes.

DE 3 244 972-C1 discloses a continuous process for producing high-purity aluminium alcoholates. According to said publication, aluminium metal is reacted with alcohol yielding aluminium alcoholate which can be liberated from other metals present in the aluminium metal by filtration and/or distillation because said metals are not converted or are only slowly converted into metal alcoholates. Up to now, however, said process has not been applicable to magnesium because the magnesium alcoholates known in the art are not liquid and, therefore, cannot be filtered.

Furthermore, they cannot be melted without undergoing decomposition and, consequently, cannot be distilled.

EP 0 244 917 describes a process for producing soluble metal alkoxides from alkoxy alcohols in organic solvents, but no reference is made therein to a process for the production of high-purity, crystalline magnesium hydroxides having fine porosities and uniform crystallinities.

Processes for producing pure magnesium hydroxides are known in the art. For example, GB-A-667,708 suggests a three-stage process wherein the reaction is carried out with watersoluble $C_1$ or $C_2$ alcohol yielding magnesium alcoholate. In the second stage, said alcoholate is substituted for a longer-chain alcohol, the $C_1$ or $C_2$ alcohol being removed by distillation. The resultant magnesium alcoholate is then hydrolysed in stage 3 of said process.

The manufacture of magnesium alkoxy ethers from hydroxy ethers is known per se (see, for instance, U.S. Pat. No. 3,657,361). However, said patent does not teach that high-purity magnesium hydroxides having special characteristics can be obtained by hydrolysis of magnesium alkoxy ether.

Therefore, it was the object of this invention to develop a process for producing magnesium hydroxide having the following features:

The magnesium hydroxide produced according to the invention is required to have high purity, fine porosity, and uniform crystallinity.

The starting materials shall be inexpensive and readily available.

The manufacturing process shall be feasible both continuously and discontinuously.

Surprisingly, it has been found that the problems cited hereinabove can be solved when employing the process described hereinbelow.

Figure 1:
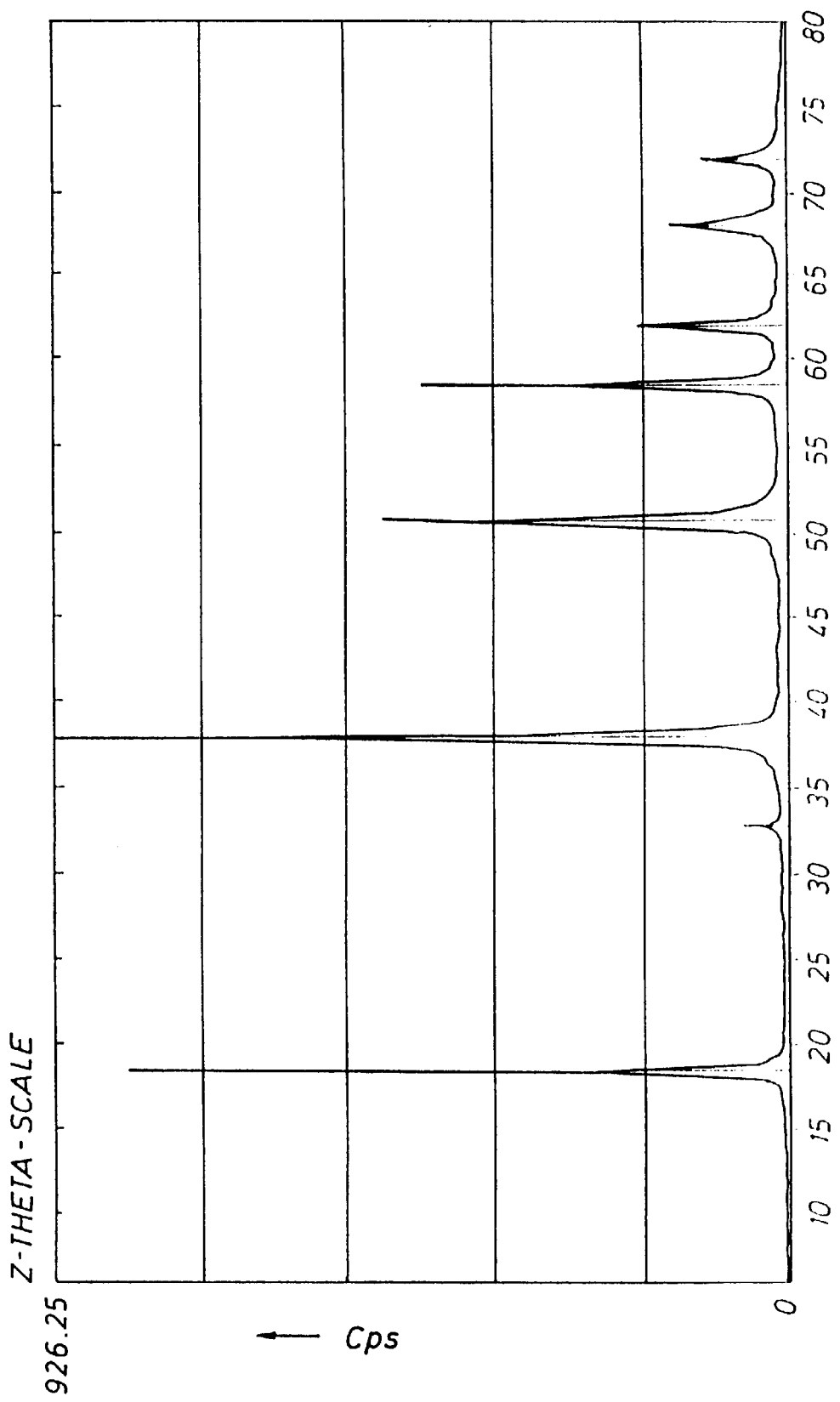
FIG. 1 is a graph showing the x-ray diffraction pattern of a magnesium hydroxide prepared according to the present invention.

The present invention refers to a process for the continuous or discontinuous production of high-purity magnesium hydroxide and/or magnesium oxide by reacting magnesium metal and reactive magnesium compounds with hydroxy compounds of the type $R^1$—A—R—OH and hydrolysing the resultant product, optionally followed by calcination if it is desirable to produce magnesium oxide. Optionally, the reaction is performed using also up to 50 percent by weight alcohols of the type $R^2$—OH.

The hydroxy compounds to be used according to the present invention have the general formula $R^1$—A—R—OH, wherein A represents an element of main group 6 of the periodic system (starting with oxygen) or main group 5 of the periodic system (starting with nitrogen). If A represents the nitrogen group, A may bear additional substituents, preferably a total of three, for saturation of its valences. These substituents can be hydrogen or an additional hydrocarbon residue $R^1$ which is optionally different from the other ones. It is preferred that the heteroatoms A be oxygen and nitrogen, oxygen being particularly preferred.

R, $R^1$, and $R^2$ represent a branched or unbranched, cyclic or acyclic, saturated, unsaturated, or aromatic hydrocarbon residue having 1 to 10 carbon atoms, wherein R, $R^1$, and $R^2$ may be different from each other and R is twofold substituted (divalent).

Preferably, $R^1$ is a saturated alkyl residue having 1 to 10 carbon atoms, particularly 1 to 5 carbon atoms, the alkyl residue being most preferably unbranched. It is preferred that $R^2$ be a branched or unbranched, cyclic or acyclic, saturated hydrocarbon residue having 4 to 8 carbon atoms, the hydrocarbon residue being most preferably unbranched, acyclic, and saturated. Preferably, R are branched or unbranched, acyclic alkylidene residues having 1 to 5 carbon atoms, unbranched hydrocarbons having 1 to 3 carbon atoms being particularly preferred.

The instant invention is based on a process for the continuous or discontinuous production of liquid magnesium alkoxides by reaction of suitable hydroxy compounds with magnesium compounds and/or magnesium metal which are reactive for said hydroxy compounds. For example, a suitable reactive magnesium compound is magnesium hydride. Magnesium metal is a particularly preferred material. It was surprisingly found that when reacting organic compounds of type $R^1$—A—R—OH with magnesium or reactive magnesium compounds, the resultant magnesium alkoxides are already liquid at room temperature.

The present invention also comprises the continuous or discontinuous hydrolysis of said liquid magnesium alkoxides, particularly magnesium alkoxy ethers and magnesium alkoxy amines, which is carried out after difficultly soluble impurities have been separated, e. g. by filtration, centrifugation, or decantation, for preparing high-purity magnesium hydroxide. After hydrolysis, there is achieved good phase separation between the water/magnesium hydroxide mixture and the alcohol components, when compounds which are free from foreign metal ions and which are suitable for salting-out, particularly 0.1 to 10 percent by weight ammonium hydrogen carbonate are added to the water for hydrolysis.

The hydroxy compounds of type $R^1$—A—R—OH referred to hereinabove can be used alone (one compound) or as a mixture (several compounds of type $R^1$—A—R—OH). Particularly if higher-viscous compounds are formed by the reaction of this invention, sedimentation of impurities which are difficultly soluble solids is impeded. In this case, the hydroxy compounds may be used in a one- to fivefold excess in order to reduce the viscosity and thus enhance filterability. For this purpose also alcohols of type $R^2$—OH can be used or can be used in larger quantities. The viscosity of the liquid/solution is most preferably adjusted by subsequent addition of $R^2$—OH alcohols.

Prior to or after reaction, part of the $R^1$—A—R—OH hydroxy compounds used for the reaction can be substituted for other alcohols, i. e. those of the $R^2$—OH type. However, the total amount of said $R^2$—OH alcohols must not be higher than 50 percent by weight, referring to the total quantity of educts and solvents to be used.

In principle, the reaction of hydroxy compounds with magnesium compounds can also be carried out using solvents. However, use of such solvents will involve higher production cost because they must be removed after conversion and, what is even more important, foreign solvents will have an adverse effect on the material properties of magnesium hydroxides, i. e. purity, uniform pore distribution, and crystallinity. Furthermore, when using foreign solvents, magnesium compounds often become solid and insoluble after conversion and purification making subsequent dissolution in a nonpolar solvent necessary before the solution can be subjected to hydrolysis. When using other solvents for the reaction, amorphous magnesium hydroxides are obtained.

Magnesium alkoxy compounds which are suitable for the production of high-purity magnesium hydroxide according to this invention include for example the experimental products bis(ethylglycolato)-magnesium (VP 1), bis(n-butyl-glycolato)-magnesium (VP 2), magnesium-bis(N,N-dimethylamino-1-propanolate) (VP 3), magnesium-bis(N,N-dimethylaminoethanolate) (VP 4), magnesium-bis(2-ethylaminoethanolate) (VP 5), or magnesium-bis(1-methoxy-2-propanolate) (VP 6).

The magnesium hydroxide produced according to this invention has high purity. In particular, the alkali and alkaline-earth metal contents which have particularly unfavorable effects in catalytic applications are very low. The results of trace elements determinations by ICP are listed in Table 1. For comparison, premium-grade magnesium hydroxide of highest purity and reagent-grade magnesium oxide, both commercially available, were included in the examinations.

TABLE 1

Trace Elements Determinations by ICP

| Compound | Fe [ppm] | Si [ppm] | Ti [ppm] | Mn [ppm] | Zn [ppm] | Ga [ppm] | Na [ppm] | Ca [ppm] |
| --- | --- | --- | --- | --- | --- | --- | --- | --- |
| Magnesium | 286 | 46 | 3 | 8 | 23 | <5 | 23 | 9 |
| Mg-alkoxide | <2 | <2 | <1 | <1 | <2 | <5 | <2 | |
| Mg(OH)$_2$ a | 12 | <2 | 3 | 3 | <2 | <5 | 14 | 6 |
| Mg(OH)$_2$ b | 52 | 699 | 1 | 7 | 2 | <5 | 58 | 2,290 |
| MgO c | 9 | 51 | 1 | 6 | 2 | 4 | 1,375 | 168 |
| MgO d | 15 | 7 | 3 | 3 | <2 | <5 | 16 | 10 |

Legend
Mg-alkoxide = bis(ethylglycolato)-magnesium
a = magnesium hydroxide prepared according to this invention
b = reference substance, premium purity (manufacturer: E. Merck AG, Darmstadt)
c = reference substance, reagent grade (manufacturer: Riedel de Haën AG, Hannover)
d = MgO prepared according to this invention from Mg(OH)$_2$ When comparing the impurities in the magnesium metal and the impurities in the magnesium alkoxide compound prepared therefrom, it becomes apparent that the separation of impurities, e. g. other metals, is performed in a highly efficient way. High-purity magnesium oxides or hydroxides within the meaning of the present invention are those products reaching the threshold values listed in Table 2.

TABLE 2

Threshold Values

| Compound | Fe [ppm] | Si [ppm] | Ti [ppm] | Mn [ppm] | Zn [ppm] | Ga [ppm] | Na [ppm] | Ca [ppm] |
| --- | --- | --- | --- | --- | --- | --- | --- | --- |
| | <50 | <50 | <10 | <10 | <10 | <10 | <50 | <50 |

In particular, the threshold values listed in Table 3 characterise high-purity products, the low concentrations of alkali ions and alkaline-earth ions, particularly Na and Ca, being most essential and making said materials very useful for a large number of catalytic applications which are very sensitive to alkali and alkaline-earth foreign ions.

TABLE 3

| Compound | Threshold Values | | | | | | | |
|---|---|---|---|---|---|---|---|---|
| | Fe [ppm] | Si [ppm] | Ti [ppm] | Mn [ppm] | Zn [ppm] | Ga [ppm] | Na [ppm] | Ca [ppm] |
| | <20 | <20 | <5 | <5 | <5 | <5 | <20 | <20 |

The purities shown in Table 1 can be further increased by using bidistilled water and containers made of inert materials. When using deionised water for the hydrolysis, the Fe, Mn, Ti, Na, and Ca concentrations in $Mg(OH)_2$ (compound a) slightly increase as compared with the magnesium alkoxide feedstock (Mg-alkoxide).

FIG. 1 represents the X-ray diffraction pattern of magnesium hydroxide prepared according to this invention. For comparison, the diffraction pattern of the JCPDS file (no. 7-0239, $Mg(OH)_2$, brucite, syn) is shown as well.

Metal oxides can be obtained by calcination of the compounds prepared according to this invention. The compounds of this invention were calcined in a furnace at temperatures of 550 to 1,500° C. for a period of 3 to 24 hours. The metal oxide prepared in this way has the same high purity as the metal hydroxide of this invention.

In Table 4 several physical data of the magnesium hydroxide prepared according to this invention have been compiled.

TABLE 4

Physical Data of Experimental Product VP 1

| $H_2O$: Alcoholate [g/g] | Surface [m²/g] | Pore Volume [ml/g] | Pore Radius [Å] | Water for Hydrolysis [pH] | Temperature of Water for Hydrolysis [° C.] |
|---|---|---|---|---|---|
| 0.15:1 | 142 | 0.71[1] | 94 | 7 | 90 |
| 2:1 | 123 | 0.62[1] | 68 | 7 | 90 |
| 4:1 | 142 | 0.62[2] | 88 | 7 | 90 |
| 4:1 | 97 | 0.76[1] | 283 | 1 | 90 |
| 4:1 | 131 | 0.40[1] | 78 | 4 | 90 |

Legend
[1] measurement by mercury porosimetry (Autopore II 9220 porosimeter, Micromeritics)
[2] measurement by nitrogen porosimetry (ASAP 2010 porosimeter, Micromeritics)

Based on the assumption that the pore radius correlates with the crystallite size, it becomes apparent that the desired pore radius and, thus, the desired crystallite size of the magnesium hydroxide of this invention can be obtained by adjusting the pH-value of the water for hydrolysis, e.g., by addition of ammonia to the water for hydrolysis.

Figure 2:
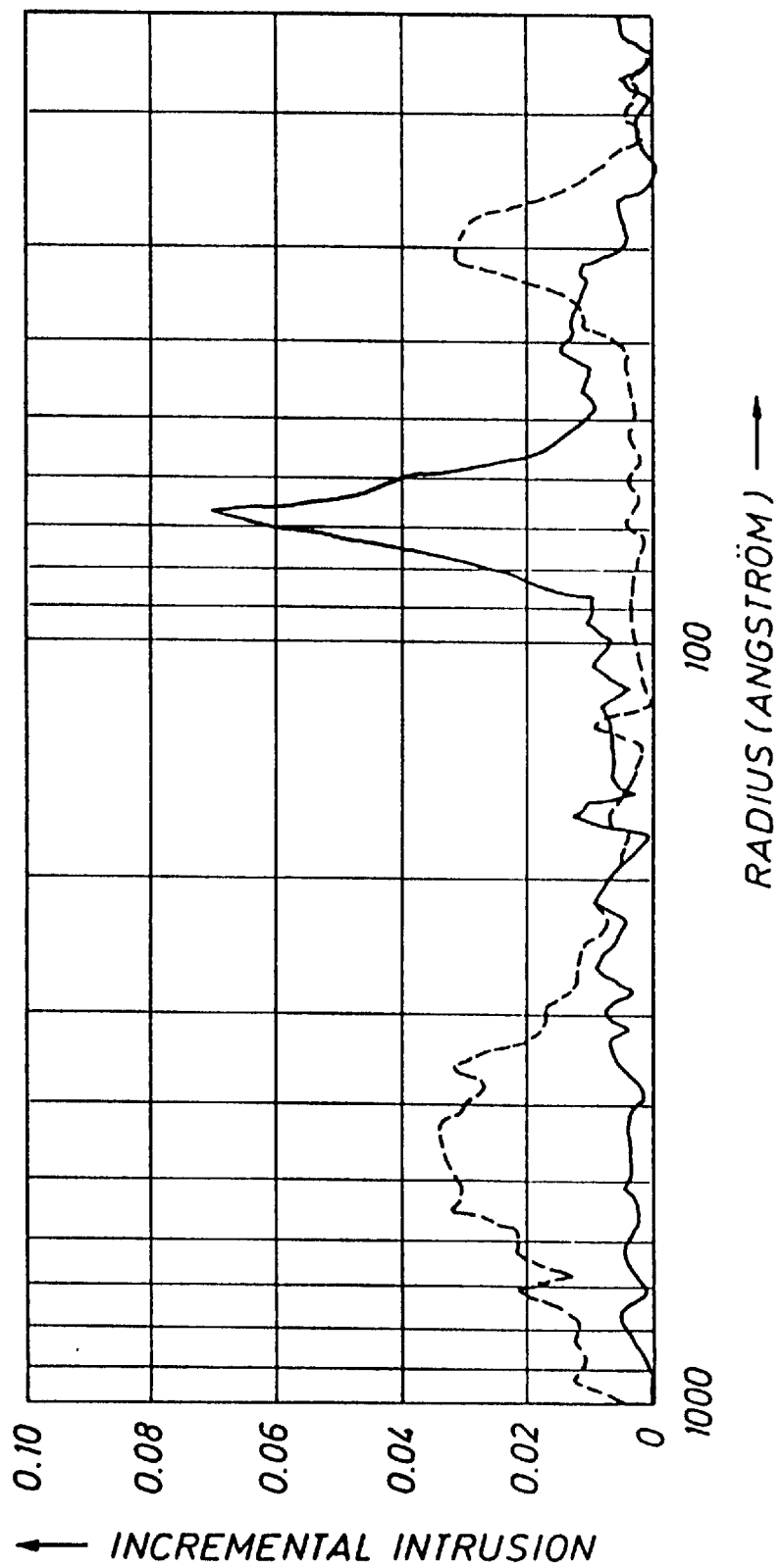
FIG. 2 is a graph showing a comparison of pore radius distribution of a prior art magnesium hydroxide and magnesium hydroxide prepared according to the present invention.
Figure 3:
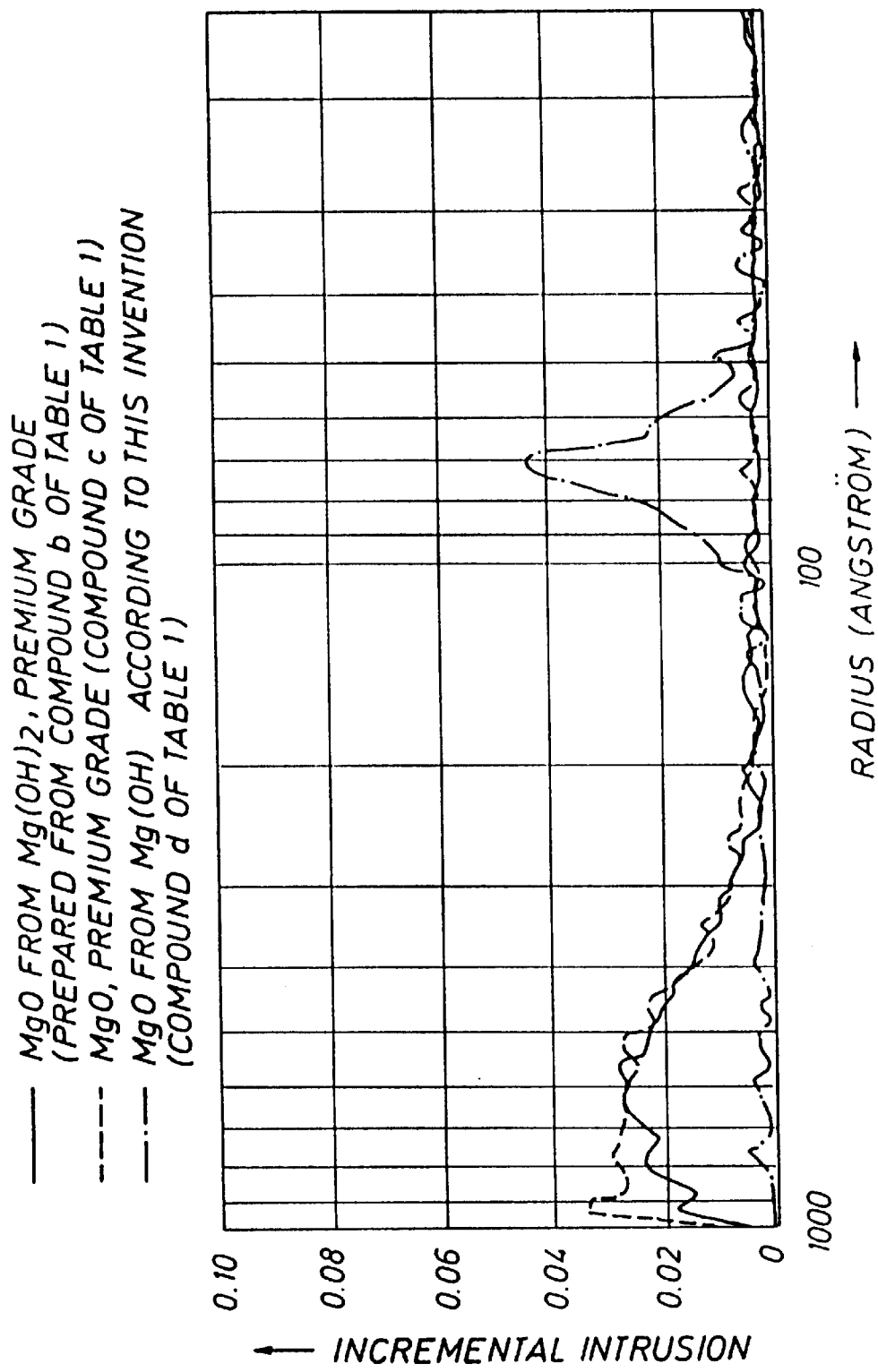
FIG. 3 is a graph comparing pore radius distribution of a magnesium oxide prepared according to the present invention with prior art magnesium oxides.

The magnesium hydroxides and oxides of this invention have significantly narrower and more uniform pore distributions (monomodal distributions) than conventional, commercially available products of this kind. For comparison, the pore distributions of magnesium hydroxide and oxide are shown in FIGS. 2 and 3. Precisely defined pore radii and narrow pore distributions have great importance in catalytic applications.

The trace impurities in the compounds of this invention were determined by inductively coupled plasma spectroscopy (ICP), while the crystalline phases were determined by powder diffractometry. The surfaces were determined by the BET method, while pore volumes and radii were additionally determined by mercury porosimetry and nitrogen porosimetry. The compounds of this invention were calcined in a muffle furnace at temperatures of between 550° C. and 1,500° C. Deionised water was used for the hydrolysis.

EXAMPLE 1

Reaction with Ethyl Glycol (Stoichiometric Amounts of $CH_3$—$CH_2$—O—$CH_2$—$CH_2$—OH); Ammoniacal Hydrolysis (VP 1)

Into a 1,000-ml three-neck flask, there were placed 20 grams of granular magnesium to which 48.4 grams of ethyl glycol were added. The mixture was heated. Reaction of the metal with ethyl glycol started at approx. 125° C. (perceptible by the formation of hydrogen and a temperature increase to approx. 140° C.). Then, 100 grams of ethyl glycol were added during a period of 30 minutes using a dropping funnel. The liquid reaction mixture was filtered, and 100 grams of the filtrate divided into three aliquot portions were hydrolysed in a $H_2O$/alcoholate mixture (4:1) consisting of 400 grams of deionised water containing 0.2 percent by weight ammonia (T=90° C.). Hydrolysis resulted in immediate formation of white precipitate. The released alcohol was distilled off, and the resultant suspension was spray dried. The yield was equal to 98% of theoretical.

EXAMPLE 1a

Reaction with Ethyl Glycol (VP 1)

Into a 1,000-ml three-neck flask, there were placed 20 grams of granular magnesium to which 50 grams of ethyl glycol were added. The mixture was heated. Reaction of the metal with ethyl glycol started at approx. 125° C. (perceptible by the formation of hydrogen and a temperature increase to approx. 140° C.). Then, 236 grams of ethyl glycol were added during a period of 50 minutes using a dropping funnel. The reaction mixture was filtered, and 100 grams of the filtrate divided into three aliquot portions were hydrolysed in a $H_2O$/alcoholate mixture (4:1) consisting of 400 grams of deionised water containing 0.2 percent by weight ammonia (T=90° C.). A white precipitate formed immediately. The released alcohol was distilled off, and the resultant suspension was spray dried. The yield was equal to 98% of theoretical.

EXAMPLE 2

Reaction with Ethyl Glycol and Hexanol; Ammoniacal Hydrolysis (VP 1)

Into a 1,000-ml three-neck flask, there were placed 20 grams of granular magnesium to which 20 grams of a hexanol/ethyl glycol mixture (50:50 percent by weight) were added. The mixture was heated. Reaction of the metal with the hexanol/ethyl glycol mixture started at approx. 125° C. (perceptible by the formation of hydrogen and a temperature increase to approx. 140° C.). Then, 266 grams of the hexanol/ethyl glycol mixture were added during a period of 50 minutes using a dropping funnel. The reaction mixture which was still liquid at room temperature was filtered, and 100 grams of the filtrate divided into three aliquot portions were hydrolysed in a $H_2O$/alcoholate mixture (4:1) consisting of 400 grams of deionised water containing 0.2 percent by weight ammonia (T=90° C.). A white precipitate formed immediately. The released alcohol was distilled off, and the resultant suspension was spray dried. The yield was equal to 98% of theoretical.

EXAMPLE 3

Reaction with n-Butyl Glycol ($CH_3$—$CH_2$—$CH_2$—$CH_2$—O—$CH_2$—$CH_2$—OH) Ammoniacal Hydrolysis (VP 2)

Into a 1,000-ml three-neck flask, there were placed 15 grams of granular magnesium to which 15 grams of n-butyl glycol were added. The mixture was heated. Reaction of the metal with n-butyl glycol started at approx. 150° C. (perceptible by the formation of hydrogen). The reaction temperature increased to approx. 180° C. Then, 252 grams of n-butyl glycol were added during a period of 90 minutes using a dropping funnel. The reaction mixture was filtered, and 100 grams of the filtrate divided into three aliquot portions were hydrolysed in a $H_2O$/alcoholate mixture (4:1) consisting of 400 grams of deionised water containing 0.2 percent by weight ammonia (T=90° C.). A white precipitate formed immediately. The released alcohol was distilled off, and the resultant suspension was spray dried. The yield was equal to 98% of theoretical.

EXAMPLE 3a

Reaction with n-Butyl Glycol (Stoichiometric Amount); Hydrolysis Without Ammonia (VP 2)

Into a 1,000-ml three-neck flask, there were placed 15 grams of granular magnesium to which 25.7 grams of n-butyl glycol were added. The mixture was heated. Reaction of the metal with n-butyl glycol started at approx. 155–160° C. (perceptible by the formation of hydrogen). Then, 120 grams of n-butyl glycol were added during a period of 90 minutes using a dropping funnel. The liquid reaction mixture was filtered, and 100 grams of the filtrate divided into three aliquot portions were hydrolysed in a $H_2O$/alcoholate mixture (4:1) consisting of 400 grams of deionised water (T=90° C.). A white precipitate formed immediately. The released alcohol was distilled off, and the resultant suspension was spray dried. The yield was equal to 98% of theoretical.

EXAMPLE 3b

Reaction with n-Butyl Glycol; Hydrolysis Without Ammonia (VP 2)

Into a 1,000-ml three-neck flask, there were placed 15 grams of granular magnesium to which 15 grams of n-butyl glycol were added. The mixture was heated. Reaction of the metal with n-butyl glycol started at approx. 155–160° C. (perceptible by the formation of hydrogen). Then, 252 grams of n-butyl glycol were added during a period of 90 minutes using a dropping funnel. The reaction mixture was filtered, and 100 grams of the filtrate divided into three aliquot portions were hydrolysed in a $H_2O$/alcoholate mixture (4:1) consisting of 400 grams of deionised water (T=90° C.). A white precipitate formed immediately. The supernatant alcohol was distilled off, and the resultant suspension was spray dried. The yield was equal to 98% of theoretical.

EXAMPLE 4

Reaction with 3-Dimethylamino-1-propanol (VP 3)

Into a 1,000-ml three-neck flask, there were placed 15 grams of granular magnesium to which 50 grams of 3-dimethylamino-1-propanol were added. The mixture was heated. Reaction of the metal with 3-dimethylamino-1-propanol started at approx. 150–160° C. (perceptible by the formation of hydrogen). Then, 197 grams of 3-dimethylamino-1-propanol were added during a period of 6 hours using a dropping funnel. The reaction mixture was filtered, and 100 grams of the filtrate divided into three aliquot portions were hydrolysed in a $H_2O$/alcoholate mixture (4:1) consisting of 400 grams of deionised water (T=90° C.). A white precipitate formed immediately. The released alcohol was distilled off, and the resultant suspension was spray dried. The yield was equal to 95% of theoretical.

EXAMPLE 5

Reaction with 2-(Dimethylamino)ethanol (VP 4)

Into a 1,000-ml three-neck flask, there were placed 15 grams of granular magnesium to which 50 grams of 2-(dimethylamino)ethanol were added. The mixture was heated. Reaction of the metal with 2-(dimethylamino)ethanol started at approx. 135–145° C. (perceptible by the formation of hydrogen). Then, 321 grams of 2-(dimethylamino)ethanol were added during a period of 5 hours using a dropping funnel. The reaction mixture was filtered, and 100 grams of the filtrate divided into three aliquot portions were hydrolysed in a $H_2O$/alcoholate mixture (4:1) consisting of 400 grams of deionised water (T=90° C.). A white precipitate formed immediately. The released alcohol was distilled off, and the resultant suspension was spray dried. The yield was equal to 96% of theoretical.

EXAMPLE 6

Reaction with 2-Ethylamino-ethanol (VP 5)

Into a 1,000-ml three-neck flask, there were placed 15 grams of granular magnesium to which 50 grams of 2-ethylamino-ethanol were added. The mixture was heated. Reaction of the metal with 2-ethylamino-ethanol started at approx. 150–160° C. (perceptible by the formation of hydrogen). Then, 123 grams of 2-ethylamino-ethanol were added during a period of 4 hours using a dropping funnel. The reaction mixture was filtered, and 100 grams of the filtrate divided into three aliquot portions were hydrolysed in a $H_2O$/alcoholate mixture (4:1) consisting of 400 grams of deionised water (T=90° C.). A white precipitate formed immediately. The released alcohol was distilled off, and the resultant suspension was spray dried. The yield was equal to 94% of theoretical.

EXAMPLE 7

Reaction with 1-(Methoxy)propan-2-ol (VP 6)

Into a 500-ml three-neck flask, there were placed 10 grams of granular magnesium to which 15 grams of 1-(methoxy)propan-2-ol were added. The mixture was heated. Reaction of the metal with 1-(methoxy)propan-2-ol started at approx. 120° C. (perceptible by the formation of hydrogen). Then, 59.1 grams of 1-(methoxy)propan-2-ol were added during a period of 5 hours using a dropping funnel. The reaction mixture was filtered, and 50 grams of the filtrate divided into three aliquot portions were hydrolysed in a H₂O/alcoholate mixture (4:1) consisting of 200 grams of deionised water (T=90° C.). A white precipitate formed immediately. The released alcohol was distilled off, and the resultant suspension was spray dried. The yield was equal to 80% of theoretical.

What is claimed is:

1. A process for producing high-purity magnesium hydroxide comprising reacting magnesium compounds metal and/or reactive magnesium compounds with at least one hydroxy reactant having the formula:

$$R^1\text{—}A\text{—}R\text{—}OH \qquad (I)$$

optionally jointly together with up to 50 percent by weight of one or more alcohol reactants having the formula:

$$R^2\text{—}OH \qquad (II)$$

wherein
   (a) A represents an element of Group VIA or Group VA of the Periodic Table, wherein if A represents an element of Group VA, A contains additional substituents selected from the group consisting of $R^1$ and hydrogen;
   (b) R and $R^1$ represent a branched or unbranched, cyclic or acyclic, saturated, unsaturated, or aromatic hydrocarbon residue having from 1 to 10 carbon atoms, wherein R and $R^1$ may be different from each other and R is twofold substituted; and
   (c) $R^2$ represents a branched or unbranched, cyclic or acyclic, saturated, unsaturated, or aromatic hydrocarbon residue having from 1 to 10 carbon atoms to form dissolved magnesium alkoxides;

separating less soluble impurities from said liquid and/or dissolved magnesium alkoxides prior to hydrolysis; and subsequently hydrolyzing said magnesium alkoxides in the substantial absence of solvents other than any remaining reactants to form magnesium hydroxides containing less than 50 ppm sodium, less than 50 ppm calcium, and having a uniform pore size distribution.

2. A process according to claim 1, characterized in that magnesium metal is used.

3. A process according to claim 1 wherein R and $R^1$ are branched or unbranched, saturated hydrocarbon residues having 1 to 5 carbon atoms and R and $R^1$ may be different from each other and R is twofold substituted.

4. A process according to claim 1, wherein the hydroxy compounds of type $R^1$—A—R—OH (I) are jointly reacted with up to 50 percent by weight of one or more alcohols of the type $$R^2\text{—}OH \qquad (II)$$

wherein $R^2$ represents a branched or unbranched, cyclic or acyclic, saturated, unsaturated, or aromatic hydrocarbon residue having 1 to 10 carbon atoms.

5. A process according to claim 4, wherein the hydroxy compounds are employed in a one- to fivefold excess based on the stoichiometric ratio of hydroxy groups to Mg valences.

6. A process according to any one of claims 2 and 4, wherein the hydroxy compounds of formula $R^2$—OH (II) are added not until after the reaction of the metal/metal compound with the hydroxy compounds of formula $R^1$—A—R—OH (I).

7. A process for producing high-purity magnesium oxide comprising reacting magnesium metal and/or reactive magnesium compounds with at least one hydroxy reactant having the formula $$R^1\text{—}A\text{—}O\text{—}H \qquad (I)$$

optionally jointly together with up to 50 percent by weight of one or more alcohol reactants having the formula $$R^2\text{—}OH \qquad (II)$$

wherein
   (a) A represents an element of group VIA or group VA of the periodic table, wherein if A represents an element of group VA, A contains additional substituents selected from the group consisting of $R^1$ and hydrogen;
   (b) R and $R^1$ represent a branched or unbranched, cyclic or acyclic, saturated, unsaturated, or aromatic hydrocarbon residue having 1 to 10 carbon atoms, wherein R and $R^1$ may be different from each other and R is twofold substituted; and
   (c) $R^2$ represents a branched or unbranched, cyclic or acyclic, saturated, unsaturated, or aromatic hydrocarbon residue having 1 to 10 carbon atoms to form liquid and/or dissolved magnesium alkoxides;

separating less soluble impurities from said magnesium alkoxides prior to hydrolysis and subsequently hydroxylyzing said magnesium alkoxides in the substantial absence of solvents, other than any remaining reactants, to form the magnesium hydroxides containing less than 50 ppm sodium and less than 50 ppm calcium and having a uniform pore size distribution; and calcinating the obtained magnesium hydroxides to form magnesium oxides having a uniform pore size distribution.

8. A process according to any one of claims 1 and 7, characterised in that $R^2$ represents an unbranched, acyclic, and saturated hydrocarbon residue having 4 to 8 carbon atoms.

9. The process of claim 1 or 7 wherein A represents an element of Group VIA of the Periodic Table.

10. The process of claim 1 or 7 wherein A represents an element of Group VA of the Periodic Table.

* * * * *

UNITED STATES PATENT AND TRADEMARK OFFICE
CERTIFICATE OF CORRECTION

PATENT NO.   : 6,569,399 B2
DATED        : May 27, 2003
INVENTOR(S)  : Andrea Brasch et al.

It is certified that error appears in the above-identified patent and that said Letters Patent is hereby corrected as shown below:

<u>Column 9,</u>
Line 8, delete the word "compounds" after the word "magnesium".

Signed and Sealed this

Twenty-first Day of October, 2003

JAMES E. ROGAN
*Director of the United States Patent and Trademark Office*